United States Patent
Chapdelaine et al.

(10) Patent No.: US 6,841,680 B2
(45) Date of Patent: Jan. 11, 2005

(54) N-TYPE CALCIUM CHANNEL ANTAGONISTS FOR THE TREATMENT OF PAIN

(75) Inventors: Marc Chapdelaine, Wilmington, DE (US); Lucius Kemp, Philadelphia, PA (US); John McCauley, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/415,783

(22) PCT Filed: Oct. 31, 2001

(86) PCT No.: PCT/SE01/02391

§ 371 (c)(1),
(2), (4) Date: Oct. 15, 2003

(87) PCT Pub. No.: WO02/36569

PCT Pub. Date: May 10, 2002

(65) Prior Publication Data

US 2004/0053965 A1 Mar. 18, 2004

(30) Foreign Application Priority Data

Nov. 6, 2000 (SE) .............................................. 0004056

(51) Int. Cl.⁷ ........................ A61K 31/47; C07D 215/22
(52) U.S. Cl. ........................ 546/159; 546/160; 546/161; 514/313
(58) Field of Search .......................... 514/313; 546/159, 546/160, 161

(56) References Cited

U.S. PATENT DOCUMENTS 5,506,235 A * 4/1996 Moyer et al. ................ 514/293

FOREIGN PATENT DOCUMENTS

WO          WO 9303030        *   2/1993

OTHER PUBLICATIONS

Marian Bala et al., "Synthesis and preliminary pharmacolo screening of 4-methylamino-2-phenylquinoline-3-carboxamides, p. 705, The Abstract No. 17614v, Pol. J. Pharmacol. Pharm. 1986, 38(1) 115–124," Chemical Abstracts, vol. 106 (No. 21), p. 705, (May 25, 1987).

* cited by examiner

*Primary Examiner*—D. Margaret Seaman
(74) *Attorney, Agent, or Firm*—Kenneth F. Mitchell

(57) ABSTRACT

Compounds having selective action at neuronal N-type calcium channels useful for the treatment of pain in accord with the following structural diagram,

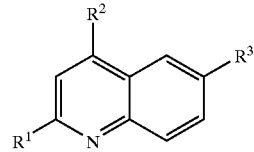

wherein $R^1$, $R^2$ and $R^3$ are a variety of groups as defined in the specification.

7 Claims, No Drawings

N-TYPE CALCIUM CHANNEL ANTAGONISTS FOR THE TREATMENT OF PAIN

This is a 371 of International Application No. PCT/SE01/02391, filed Oct. 31, 2001, which claims the priority of Application No 0004056-8 filed in Sweden on Nov. 6, 2000.

FIELD OF THE INVENTION

This invention relates to compounds and methods for the treatment or prevention of pain or nociception.

RELATED ART

Pain causes a great deal of suffering and is a sensory experience distinct from sensations of touch, pressure, heat and cold. It is often described by sufferers by such terms as bright, dull, aching, pricking, cutting or burning and is generally considered to include both the original sensation and the reaction to that sensation. This range of sensations, as well as the variation in perception of pain by different individuals, renders a precise definition of pain difficult. Where pain is "caused" by the stimulation of nociceptive receptors and transmitted over intact neural pathways, this is termed nociceptive pain. Pain may also be caused by damage to neural structures, and pain is often is manifested as neural supersensitivity; this type of pain is referred to as neuropathic pain.

The level of stimulation at which pain is perceived is referred to as the "pain threshold". Where the pain threshold is raised, for instance, by the administration of an analgesic drug, a greater intensity or more prolonged stimulus is required before pain is experienced. Analgesics are a class of pharmaceutical agent which, following administration to a patient in need of such treatment, relieve pain without loss of consciousness. This is in contrast to other pain-relieving drugs, for example, general anaesthetics which obtund pain by producing a hiatus in consciousness, or local anaesthetics which block transmission in peripheral nerve fibres thereby preventing pain.

Tachykinin antagonists have been reported to induce antinociception in animals, which is believed to be analogous to analgesia in man (for review see Maggi et al, J. Auton. Pharmacol. (1993) 13, 23–93). In particular, non-peptide NK-1 receptor antagonists have been shown to produce such analgesia, thus, for example, in classical tests of chemo-nociception (phenylbenzoquinone-induced writhing and formalin test) the NK-1 receptor antagonist RP 67,580 produced analgesia with potency comparable to that of morphine (Garret et al, Proc. Natl. Acad. Sci. USA (1993) 88, 10208–10212).

Opioid analgesics are a well-established class of analgesic agents. These compounds are generally accepted to include, in a generic sense, all drugs, natural or synthetic, with morphine-like actions. The synthetic and semi-synthetic opioid analgesics are derivatives of five chemical classes of compound: phenanthrenes; phenylheptylamines; phenylpiperidines; morphinans; and benzomorphans. Pharmacologically these compounds have diverse activities, thus some are strong agonists at the opioid receptors (e.g. morphine); others are moderate to mild agonists (e.g. codeine); still others exhibit mixed agonist-antagonist activity (e.g. nalbuphine); and yet others are partial agonists (e.g. nalorphine). Whilst an opioid partial agonist such as nalorphine, (the N-alkyl analogue of morphine) will antagonise the analgesic effects of morphine, when given alone it can be a potent analgesic in its own right. Of all of the opioid analgesics, morphine remains the most widely used and is a suitable archetype compound. Unfortunately, apart from its useful therapeutic properties, morphine also has a number of drawbacks including respiratory depression, decreased gastrointestinal motility (resulting in constipation) and, in some individuals, nausea and vomiting may occur. Another characteristic is the development of tolerance and physical dependence which may limit the clinical use of such compounds.

Anti-inflammatory compounds directed at blocking or reducing synovial inflammation, and thereby improving function, and analgesics directed to reducing pain, are presently the primary method of treating the rheumatoid diseases and arthritis. Aspirin and other salicylate compounds are frequently used in treatment to interrupt amplification of the inflammatory process and temporarily relieve the pain. Other drug compounds used for these purposes include phenylpropionic acid derivatives such as Ibuprofen and Naproxin, Sulindac, phenyl butazone, corticosteroids, antimalarials such as chloroquine and hydroxychloroquine sulfate, and fenemates. For a thorough review of various drugs utilized in treating rheumatic diseases, reference is made to J. Hosp. Pharm., 36:622 (May 1979).

Calcium channels are membrane-spanning, multi-subunit proteins that allow controlled entry of $Ca^{++}$ ions into cells from the extracellular fluid. Such channels are found throughout the animal kingdom, and have been identified in bacterial, fungal and plant cells. Commonly, calcium channels are voltage dependent. In such channels, the "opening" allows an initial influx of $Ca^{++}$ ions into the cells which lowers the potential difference between the inside of the cell bearing the channel and the extracellular medium bathing the cell. The rate of influx of $Ca^{++}$ ions into the cell depends on this potential difference. All "excitable" cells in animals, such as neurons of the central nervous system ("CNS"), peripheral nerve cells, and muscle cells, including those of skeletal muscles, cardiac muscles, and venous and arterial smooth muscles, have voltage-dependent calcium channels. Calcium channels are physiologically important because the channels have a central role in regulating intracellular $Ca^{++}$ ions levels. These levels are important for cell viability and function. Thus, intracellular $Ca^{++}$ ion concentrations are implicated in a number of vital processes in animals, such as neurotransmitter release, muscle contraction, pacemaker activity, and secretion of hormones.

It is believed that calcium channels are relevant in certain disease states. A number of compounds useful in treating various cardiovascular diseases in animals, including humans, are thought to exert their beneficial effects by modulating functions of voltage-dependent calcium channels present in cardiac and/or vascular smooth muscle. Many of these compounds bind to calcium channels and block, or reduce the rate of, influx of $Ca^{++}$ ions into the cells in response to depolarization of the cell membrane. An understanding of the pharmacology of compounds that interact with calcium channels in other organ systems, such as the central nervous system, and the ability to rationally design compounds that will interact with these specific subtypes of human calcium channels to have desired therapeutic, e.g., treatment of neurodegenerative disorders, effects have been hampered by an inability to independently determine how many different types of calcium channels exist or the molecular nature of individual subtypes, particularly in the CNS, and the unavailability of pure preparations of specific channel subtypes, i.e., systems to evaluate the specificity of calcium channel-effecting compounds.

Multiple types of calcium channels have been detected based on electrophysiological and pharmacological studies of various mammalian cells from various tissues (e.g., skeletal muscle, cardiac muscle, lung, smooth muscle and brain) Bean, B. P., Annu Rev. Physiol. 51:367–384 (1989) and Hess, P., Annu. Rev. Neurosci. 56:337 (1990). These different types of calcium channels have been broadly categorized into four classes, L-, T-, N-, and P-type, distinguished by current kinetics, holding potential sensitivity and sensitivity to calcium channel agonists and antagonists. Four subtypes of neuronal voltage-dependent calcium channels have been proposed Swandulla, D. et al., Trends Neurosci 14:46 (1991). The L-, N- and P-type channels have each been implicated in nociception, but only the N-type channel has been consistently implicated in acute, persistent and neuropathic pain. A synthetic version of ω-conotoxin MVIIA, a 25-amino acid peptide derived from the venom of the piscivorous marine snail, *Conus magus* has been used intrathecally in humans and has ~85% success rate for the treatment of pain with a greater potency than morphine.

While known drug therapies have utility, there are drawbacks to their use. For instance, it may take up to six months of consistent use of some medications in order for the product to have effect in relieving the patient's pain. Consequently, a particular subject may be receiving treatment and continuing to suffer for up to six months before the physician can assess whether the treatment is effective. Many existing drugs also have substantial adverse side effects in certain patients, and subjects must therefore be carefully monitored. Additionally, most existing drugs bring only temporary relief to sufferers and must be taken consistently on a daily or weekly basis for continued relief. Finally, with disease progression, the amount of medication needed to alleviate the pain may increase thus increasing the potential for side effects. Thus, there is still a need for an effective and safe treatment to alleviate pain.

SUMMARY OF THE INVENTION

In one aspect the present invention provides compounds having selective action at N-type calcium channels that are useful for the treatment of pain.

Compounds of the present invention that show selective action at N-type calcium channels are compounds in accord with structural diagram I,

I wherein:
$R^1$ is halophenyl;
$R^2$ is $NE^1E^2$ where $E^1$ is selected from hydrogen and $C_{1-3}$alkyl and $E^2$ is selected from $C_{1-3}$alkyl and $(CH_2)_n$phenyl where n is selected from 1, 2 or 3, and
$R^3$ is selected from phenyl, 1,3-benzodioxolyl and phenyl substituted with one, two or three moieties independently selected from halo, $C_{1-3}$alkyl, perhalo$C_{1-3}$akyl, HC(O)—, $C_{1-3}$alkoxy and $C_{1-3}$alkylcarbonyl.

Particular compounds of the inventions are those wherein:
$R^1$ is fluorophenyl;
$R^2$ is $NE^1E^2$ where $E^1$ is selected from hydrogen and methyl, and $E^2$ is methyl, and
$R^3$ is selected from phenyl, 1,3-benzodioxol-5-yl and phenyl substituted with one, two or three moieties independently selected from chloro, fluoro, methyl, ethyl, methoxy, ethoxy, trifluoromethyll, HC(O)—, and $CH_3C(O)$—.

More particular compounds of the invention are those wherein:
Particular compounds of the inventions are those wherein:
$R^1$ is 3-fluorophenyl;
$R^2$ is $NE^1E^2$ where $E^1$ is selected from hydrogen and methyl, and E is methyl, and
$R^3$ is selected from phenyl, 1,3-benzodioxol-5-yl and phenyl substituted with one, two or three moieties independently selected from chloro, fluoro, methyl, ethyl, methoxy, ethoxy, trifluoromethyll, HC(O)—, and $CH_3C(O)$—.

Most particular compounds of the invention are those exemplified herein.

In another aspect, the invention comprises a method for using compounds according to structural diagram I for the treatment of pain, said method comprising administering a pain-ameliorating effective amount of any such compound.

One embodiment of the method of the invention comprises administering a pain-ameliorating effective amount of a compound in accordance with structural diagram I to a subject in need of treatment for acute, persistent or neuropathic pain.

In a further aspect, the invention comprises methods for making compounds in accord with structural diagram I.

In yet another aspect, the invention comprises pharmaceutical compositions comprising compounds in accord with structural diagram I together with excipients, diluents or stabilisers, as further disclosed herein, useful for the treatment of acute, persistent and neuropathic pain.

DETAILED DESCRIPTION OF THE INVENTION

Compounds of the invention are those within the scope of the generic description and particularly those compounds exemplified hereafter.

Suitable pharmaceutically-acceptable salts of compounds of the invention include acid addition salts such as methanesulphonate, karate, hydrochloride, hydrobromide, citrate, tris(hydroxymethyl)aminomethane, maleate and salts formed with phosphoric and sulphuric acid.

Where compounds of the present invention possess a chiral center it is to be understood that the invention encompasses all optical isomers and diastereoisomers of such compounds.

Where compounds of the present invention can tautomerize it is to be understood that the invention encompasses all tautomeric forms of such compounds.

Where compounds of the present invention can exist in unsolvated as well as solvated forms such as, for example, hydrated forms, it is to be understood that the invention encompasses all such solvated and unsolvated forms.

Another aspect of the invention provides processes for making compounds of the invention, as follows:

a) reacting a substituted acetophenone according to structural diagram II with acetic anhydride and sodium hydride to form a 3-oxo-propionic acid ethyl ester according to structural diagram III, as follows:

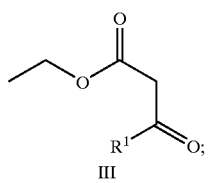

b) reacting a compound of structural diagram III with 4-bromoaniline to form a 3-substituted 3-(4-bromophenylamino)acrylic acid butyl ester according to structural diagram IV, as follows:

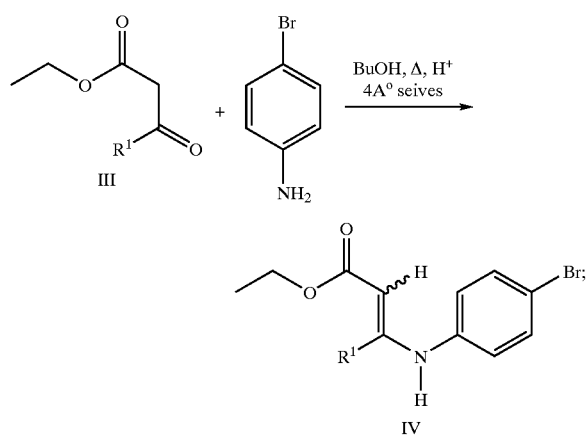

c) cyclizing a compound of structural diagram IV to form a 2-substituted 6-bromo-4-hydroxy-quinoline according to structural diagram V, as follows:

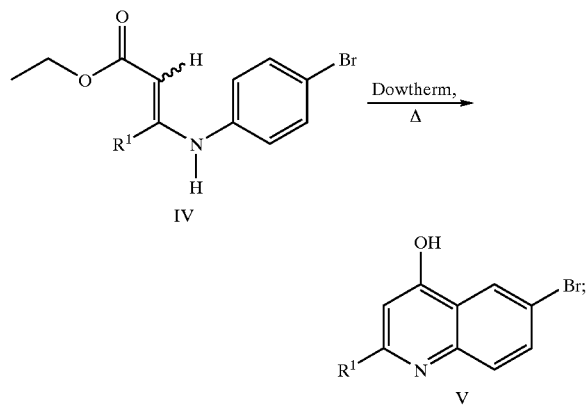

d) chlorinating a compound of structural diagram V to form a compound according to structural diagram VI, as follows:

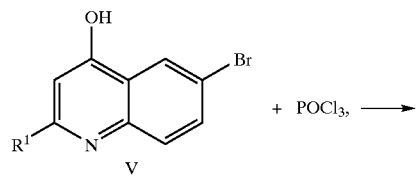

e) selectively replacing the chlorine moiety of a compound of structural diagram VI to form a compound according to structural diagram VII, as follows:

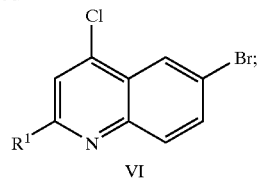

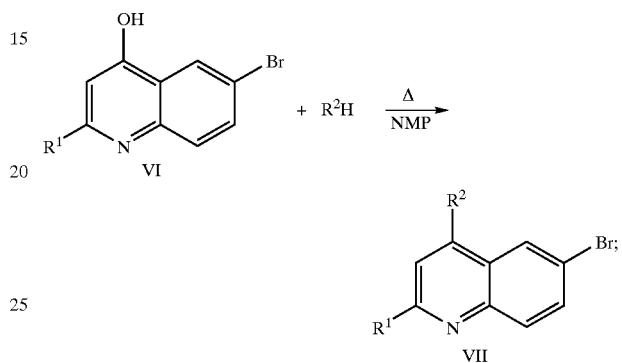

f) selectively replacing the bromine moiety of a compound of structural diagram VII by reaction with a substituted boronic acid to form a compound according to structural diagram I, as follows:

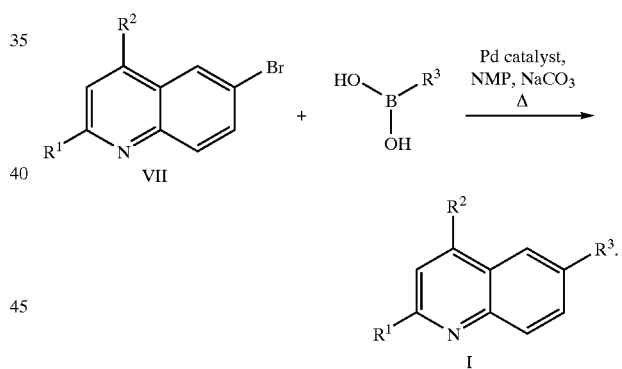

wherein, if necessary, in steps a), b), c), d), e) and f) any functional group is protected with a protecting group, and thereafter, g) removing any said protecting group;

h) converting one compound according to structural diagram I to another compound according to structural diagram I by procedures described in Methods A through L herein, and i) purifying said compound of structural diagram I to the extent necessary and, if necessary, forming a pharmaceutically-acceptable salt.

To use a compound of the invention or a pharmaceutically-acceptable salt thereof for the therapeutic treatment, which may include prophylactic treatment, of pain in mammals, which may be humans, the compound can be formulated in accordance with standard pharmaceutical practice as a pharmaceutical composition. Accordingly, a further aspect of the invention provides a pharmaceutical composition which contains a compound of the structural diagram I as defined herein or a pharmaceutically-acceptable salt thereof, in association with a pharmaceutically-acceptable additive such as an excipient or carrier.

Suitable pharmaceutical compositions that contain a compound of the invention may be administered in conventional ways, for example by oral, topical, parenteral, buccal, nasal, vaginal or rectal administration, or by inhalation. For these purposes a compound of the invention may be formulated by means known in the art in the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solutions or suspensions or sterile emulsions. A preferred route of administration is orally by tablet or capsule.

In addition to a compound of the present invention, a pharmaceutical composition of this invention may also contain one or more other pharmacologically-active agents. Alternatively, a pharmaceutical composition comprising a compound of this invention may be co-administered simultaneously or sequentially with one or more other compatible pharmacologically-active agents.

Pharmaceutical compositions of this invention will normally be administered so that a pain-ameliorating effective daily dose is received by the subject. The daily dose may be given in divided doses as necessary, the precise amount of the compound received and the route of administration depending on the weight, age and sex of the patient being treated and on the particular disease condition being treated according to principles known in the art. A preferred dosage regime is once daily.

A yet further embodiment of the invention provide the use of a compound of the structural diagram I, or a pharmaceutically-acceptable salt thereof, in the manufacture of a medicament useful for binding to N-type calcium channels in a warm-blooded animal such as a human being.

Still another embodiment of the invention provides a method of binding a compound of the invention to N-type calcium channels of a warm-blooded animal, such as a human being, in need of treatment for pain, which method comprises administering to said animal an effective amount of a compound of structural diagram I or a pharmaceutically-acceptable salt thereof.

A further aspect of the present invention provides a pharmaceutical composition which includes a compound of the present invention as defined herein or a pharmaceutically-acceptable salt thereof, in association with a pharmaceutically-acceptable additive such as an excipient or a carrier.

A still further aspect of the present invention is a method of treatment of the human or animal body that includes the administration of a compound of the present invention or a pharmaceutically-acceptable salt thereof.

Definitions:

When used herein "halo" or "halogen" means fluoro, chloro, bromo or iodo;

when substituents herein are stated to be "selected from" or "independently selected from" a group of moieties, it is to be understood that included compounds are those where all substituents are the same and compounds where each substituent is different;

when used herein the term "alkyl," as in for example $C_{1-6}$allyl, unless otherwise defined, includes both straight and branched chain alkyl groups. References to individual alkyl groups such as "propyl" mean the normal, straight chain form, that is, n-propyl;

when used herein, a term such as "$C_{1-6}$alkyl" means alkyl groups having 1, 2, 3, 4, 5 or 6 carbon atoms and collective groups such as $C_{1-4}$alkyl and includes straight and branched moieties such as methyl, ethyl, iso-propyl and t-butyl, similarly, a term such as "$C_{1-3}$alkoxy" includes particular moieties such as methoxy, ethoxy and propoxy, and terms used herein that are not otherwise defined are intended to have their conventionally-understood meaning.

The Methods and Examples which follow are intended to illustrate but not limit the invention. In the Methods and Examples, unless otherwise stated:

concentrations were carried out by rotary evaporation in vacuo;

operations were carried out at ambient temperature, that is in the range 18–26° C. and under a nitrogen atmosphere;

column chromatography (by the flash procedure) was performed on Merck Kieselgel silica (Art. 9385);

yields are given for illustrative purposes only and are not necessarily the maximum attainable;

the structure of compounds of the invention were generally confirmed by conventional NMR and mass spectral techniques, peak multiplicities are shown thus: s, singlet; bs, broad singlet; d, doublet; AB or dd, doublet of doublets; t, triplet; dt, double of triplets; m, multiplet; bm, broad multiplet; FAB m/s data were obtained using a Platform spectrometer (supplied by Micromass) run in electrospray and, where appropriate, either positive ion data or negative ion data were collected, herein (M+H)$^+$ is provided;

purity of intermediates were was in general assessed by m/s or NMR analysis; and where used the following abbreviations have meanings as follows:

| | |
|---|---|
| DCM | is dichloromethane, |
| DMF | is N,N-dimethylformamide, |
| DMSO | is dimethylsulfoxide, |
| CDCl$_3$ | is deuterated chloroform, |
| FAB | is fast atom bombardment, |
| m/s | is mass spectroscopy or mass spectral, |
| NMR | is Nuclear Magnetic Resonance, |
| NMP | is N-methylpyrrolidinone, and |
| THF | is tetrahydrofuran. |

Biological Methods:

I. N-Channel FLIPR (Fluorescent Laser Imaging Plate Reader) Assay.

The methods described herein provide a reliable FLIPR-based readout of the efficacy and potency with which test compounds inhibit calcium flux through the N-type calcium channel expressed in its native form in a human-derived neuroblastoma cell line differentiated chemically to a neuronal phenotype. The degree to which a compound at a particular concentration inhibited the N-channel calcium flux was determined by comparing the amplitude of peak calcium increase in the presence of the compound to a control 80 mM K$^+$ stimulus in wells without compound. Results obtained for this FLIPR assay were validated in two ways:

a) the N-channel specific peptide toxin, conotoxin MVIIA, showed an IC$_{50}$=3 nM (determined from fit to five-point concentration response analysis), compatible with the known literature value; and b) IC$_{50}$ values were determined for a set of 18 small molecules from chemistry lead series (pIC$_{50}$ range: 4.67–7.02).

Potency of these same test compounds as inhibitors of the N-type calcium current was also determined by direct electrophysiological measurement either in neuronally differentiated IMR-32 cells, or in freshly-isolated rat superior cervical ganglion neurons. $pIC_{50}$'s yielded by the two methodologies for the compound set were closely comparable (r=0.91; p<0.001).

A. Cell Culture.

An immortalized cell line, IMR32, derived from human neuroblastoma cells obtained from the ATCC (product #CCL-127) was used for all experiments. Cells were grown in T75 flasks containing Eagle's minimum essential medium (MEM) w/Earle's salts and non-essential amino acids without glutamine (Cat. #SLM-034B, Specialty Media, Philipsburg, N.J.), 10% FBS and 1% glutamine. Cells were grown to ~70–80% confluency (by visual microscopic estimation) before sub-culturing. To maintain a stock culture, cultures were split at a ratio of 1:3–1:4 by creating a cell suspension by trituration, and pipetting a volume of the cell suspension sufficient to yield this final ratio into new flasks containing ~20 mL of fresh media. Sub-culturing was generally performed two times per week. For preparation of 96 well plates (black-walled; Cat #3603, Costar Co., Cambridge, Mass.), a T75 flask containing cells of desired confluency was brought up to 120 ml volume with media. Cells were then freed by trituration, and the cell suspension was plated into 12–96 well plates to yield final well volume of 100 $\mu$L.

B. Cell Differentiation to Neuronal Phenotype.

Cells were induced to differentiate in a differentiation medium consisting of: MEM, 10% FBS, 1% glutamine, 1 $\mu$M 2-butyl-cAMP (49.1 mg/100 mL media (Cat. #D-0627, Sigma Corp., St Louis, Mo.), and 2.5 mM bromo-deoxy-uridine (stock: 30.7 mg/10 mL media, 25 mL of above stock/100 mL media; Sigma Cat. #B-9285). To induce differentiation, the cells were treated with differentiation media (by complete medium change) 2 days after an initial plating in 96 well plates. Confluency at this time was ~40%. A complete medium change with freshly prepared differentiating medium was subsequently performed every 2–3 days. Cells were exposed to these differentiation conditions for 6 to 11 days before being used in FLIPR experiments.

C. Standard Experimental Solutions.

Solutions of the following composition (in mM) were used in experiments (Buffers without probenicid purchased from Specialty Media (Buffers A and B: Cat. #BSS053A; Buffers C & D: Cat. #BSS056A).

Buffer A (first wash buffer): Krebs-Ringer-HEPES (KRH) buffer: NaCl: 125, KCl: 5, $MgSO_4$: 1.2, $KH_2PO_4$: 1.2, $CaCl_2$ $2H_2O$: 2, Glucose: 6, HEPES: 25, pH: 7.4 (pH adjusted with NaOH)

Buffer B (dye loading buffer) KRH buffer with 2.5 $\mu$M probenicid: same as buffer A, but probenicid added to final concentration of 2.5 $\mu$M. Probenecid (Cat. #P-8761, Sigma Chemical Co., St. Louis, Mo.) made as a stock solution at 250 mM.

Buffer C (dye washout buffer) KRH buffer with 0 mM $K^+$ and 2.5 $\mu$M probenicid: NaCl: 130, $MgSO_4$:1.2, $NaH_2PO_4$: 1.2, $CaCl_2 2H_2O$: 6, HEPES: 25, pH; 7.4 (pH adjusted with NaOH).

Buffer D (compound dilution buffer): Buffer C with 0.1% w/v bovine serum albumin (BSA; Sigma).

D. Pharmacological Standards and Compounds.

The following solutions were used to obtain the data disclosed herein.

Nitrendipine: (RBI Chemicals, Natick, Mass.): Stock: 10 mM in DMSO; Pipetting solution: 9 $\mu$M; pipette 20 $\mu$L into 120 $\mu$L volume in well for final well concentration: 1 $\mu$M.

w-Conotoxin MVIIA: (Cat. #H-8210; Bachem Inc., Torrance, Calif.): Stock: 1 mM in HPLC grade $H_2O$ with 0.1% BSA; Pipetting solution: 4.5 $\mu$M; pipette 20 $\mu$l into 140 $\mu$l volume in well for final well concentration: 1 $\mu$M.

Test compound stock and solution preparation: Compounds prepared daily as stocks at 10 mM in 100% DMSO; Pipetting solution: 45 $\mu$M or serial dilutions thereof; pipette 20 $\mu$L into 140 $\mu$L volume in well for final well concentration: 1 $\mu$M or 10-fold dilutions thereof.

High potassium (depolarization) solution: Buffer C with 240 mM $K^+$ added; pipette 80 $\mu$L into 160 $\mu$L volume in well for final well concentration of 80 mM $K^+$.

E. Cell Loading with Fluorescent Dyes.

Fluorescent dye solution preparation: A calcium indicator dye, Fluo-4 acetylmethylester (Fluo 4-AM; Cat. #F-124201; Molecular Probes, Eugene, Oreg.) was used to measure changes in intracellular free calcium with FLIPR. 1 mM Fluo-4 AM stock solution was made by dissolution in DMSO. This stock was then diluted to 4.6 $\mu$M with Buffer B (Fluo-4 AM working solution).

Cell loading procedure: Plates containing cells were washed with Buffer A using an automated cell washer (Model #: 5161552, Labsystems Oy, Helsinki, Finland) with controls set to the following parameters: cell height: C/D; cell pulse: 4/5, washes: 3; volume: 5; DRY position setting. These settings resulted in a 70 $\mu$L residual depth of buffer over cells in each well. 100 $\mu$L of the Fluo-4 AM working solution was then added to each well resulting in a final Fluo-4 AM concentration of 2.7 $\mu$M Cells were incubated in this solution at 37° C. for 1–1.5 h. Cells were then washed with Buffer C five times using the cell washer with parameters the same as the pre-loading washes above with the exceptions of: washes: 5; WET position setting. A final wash was then conducted by changing the parameters as follows: washes: 1; volume: 2. This resulted in a final well volume of 120 $\mu$L. Cells were allowed to equilibrate under this condition for 10 min, and then used in the FLIPR protocol.

F. FLIPR Protocol

Instrumentation: Real time changes in intracellular free calcium in response to potassium-induced depolarization in the absence or presence of putative N-channel inhibitors were measured by either a FLIPR I or FLIPR II (configured for 96-well format) instrument (Molecular Devices, Sunnyvale, Calif.). Identical settings and protocols were used with each instrument, and results obtained from the two instruments were indistinguishable for a set of standard benchmark compounds.

FLIPR hardware settings: Laser power was set to about 0.3 watts. Excitation wavelength was set to a 488 nm peak, and the emission wavelength to 540 nm. Camera aperture was set to 2. All experiments were conducted at room temperature (20–22° C.).

Plate layout—reference signals: Certain wells on each plate were allocated to standards to determine minimum and maximum specific fluorescent signal against which inhibitory effects of compounds were normalized. The reference standards were distributed at plate locations including edge and interior wells Maximum signal (N-channel+non-specific): 12 wells were incubated in nitrendipine (1 $\mu$M) solution and 80 mM $K^+$ added to determine maximal $Ca^{2+}$ increase mediated by N-channels+non-specific (non-L, non-N-channel mediated fluorescence increase). The coefficient of variation amongst these wells for the $K^+$-evoked peak increase in fluorescence units was typically less than 12%.

Minimum signal (non-specific): 6 wells were incubated in nitrendipine (1 $\mu$M)+w-conotoxin MVIIA and 80 mM $K^+$ added to determine background $Ca^{2+}$ with all N-channels pharmacologically occluded. The peak non-specific signal component was typically less than 15% of the maximum signal peak amplitude.

N-channel reference small molecule: A compound that had been characterized extensively with respect to N-channel inhibitory activity in both FLIPR and patch clamp electrophysiology was included on each plate in triplicate at 1 µM (near $IC_{50}$) to establish a reference point.

Test compounds: 5 test compounds were evaluated for potency on each plate. Each compound was tested at 5 increasing concentrations spanning half-log units and typically reaching a maximal concentration of 10 µM. Each concentration was tested in triplicate wells.

Protocol structure: The FLIPR protocol was configured as three solution addition/sampling sequences (see below). Conotoxin (1 µM final conc.) was added to appropriate wells prior to placing the plate in the FLIPR instrument. Wells initially contained a total solution volume of 100 µl, and after all three solution additions contained 240 µl. The active mixing (by the pipette) option was not used in any sequence.

Nitrendipine addition sequence: 28 s total duration with fluorescence signal sampling at 1 Hz for 2 s, followed by addition of 20 µL nitrendipine standard solution at 10 µL/s, followed by sampling at 0.5 Hz for 24 s.

Test compound addition sequence: 64 s total duration with sampling at 0.5 Hz for 4 sec, test solution addition of 40 µL at 20 µL/s, followed by sampling at 0.2 Hz for 60 s.

Compound incubation, cell depolarization and calcium readout sequence: 1024 s total duration with sampling at 0.0167 Hz for 840 s, followed by solution addition 80 µL of high $K^+$ (depolarization) solution, followed by sampling at 1 Hz for 180 sec. This final 180 sec sampling interval thus represented the epoch where the peak increase in intracellular calcium due to flux through activated N-channels occurred.

G. Data Analysis

FLIPR software: Prior to export, the data was normalized within the FLIPR software module for two effects.

Baseline correction: The baseline was corrected by "zeroing" at sample #57 (immediately prior to KCl addition). This normalization served to correct the y axis offset of the fluorescent trace from each well so that all traces had a common point just prior to onset of the relevant evoked fluorescent increase.

Spatial uniformity correction factor: The data was normalized by a procedure which calculates a mean over the plate of fluorescent units from the first sample, and then multiplies the data from each well by a scalar that adjusts the value of the first sample to this average value, thus normalizing for differences in absolute baseline fluorescence amongst the wells caused by differences in cell densities or dye loading.

External software: Data were exported from FLIPR into Excel as "*.squ" extension files. Following export, operations were performed in Excel to calculate the maximal peak amplitude (relative to the zeroed baseline) of the fluorescence increase following potassium addition in each well. Measurements from wells where an test compound was added were then normalized as a percentage between the mean amplitudes from the reference wells providing the maximum (100%) and non-specific (0%) signal components, as described above. The resulting percent inhibition by test compounds was considered to reflect inhibition of calcium flux at the N-type channel.

II. L-channel FLIPR Assay.

The methods described below provided a reliable FLIPR-based readout of the efficacy and potency with which test compounds inhibited calcium flux through the L-type calcium channel expressed natively in a human-derived neuroblastoma cell line, SK-N-SH. The degree to which a given compound concentration inhibited the L-channel was determined by comparing the amplitude of peak calcium increase to an 80 mM $K^+$ stimulus in the test well to the peak increase in wells without compound. The assay was validated by obtaining 5-point concentration-response curves and thereby determining $IC_{50}$ values for the reference L-channel blockers, nitrendipine (30 nM), nifedipine and verapamil. These values were compatible with the known literature values for these agents to block $Ca^{2+}$ flux through the L-channel, A. Cell Culture:

An immortalized cell line, SK-N-SH, derived from human neuroblastoma cells (ATCC product #HTB-11) was used for all experiments. Cells were grown in T75 flasks containing Eagle's minimum essential medium (MEM) w/Earle's salts, with 0.1 mM non-essential amino acids, 1.0 mM Na pyruvate and 10% fetal bovine serum (FBS; Cat. #SLM-034B, Specialty Media). Cells were grown to 100% confluency (by visual microscopic estimation) before sub-culture. Cells were sub-cultured at a ratio of 1:3 by first rinsing with 3 mL PBS, replacing the PBS with PBS containing 0.25% trypsin until the cells detached from the surface. 1 mL of the resulting suspension was then added to a new flask containing 10 mL fresh media. Cells were then incubated (37° C., 5% $CO_2$), and media was exchanged about 3 days after subculturing.

B. Preparation of Cells for Experiments:

Cells used for experiments were at the 100% confluency growth stage. Each flask provided enough cells for three 96-well plates. Cells were detached from the flask by addition of 0.25% trypsin, as described for the sub-culturing protocol. Once detached, 7 mL fresh media was added to the flask, and the solution triturated gently. An additional 20 mL media was then added, and 100 µL of this final cell suspension was then added to each well of a 96-well plate. Before use in experiments the plates were incubated at 37° C. in 5% $CO_2$ until cells reached 100% confluence (1–2 days).

C. Experimental Procedures:

The composition of solutions, hardware settings, plate layout, structure of the FLIPR protocol, and analytical settings and procedures were identical to those described herein for the N-channel assays with the following differences as regards Plate layout and reference signals.

Maximum signal (L-channel+non-specific): 12 wells received 20 µL buffer addition only (no nitrendipine) in the first solution addition sequence to define the maximal $K^+$-evoked $Ca^{2+}$ increase mediated by L-channels+non-specific (non-L-channel mediated fluorescence increase). The coefficient of variation amongst these wells for the $K^+$-evoked peak increase in fluorescence units was typically less than 12%.

Minimum signal (non-specific): 6 wells were incubated in nitrendipine (1 µM), followed by 80 mM $K^+$ added to determine background $Ca^{2+}$ with all L-channels pharmacologically occluded. The peak non-specific signal component was typically less than 15% of the maximum signal peak amplitude.

L-channel reference small molecule: Nitrendipine was included in triplicate wells on each plate at 30 nM (near $IC_{50}$) for a reference readout III. N-Channel Patch Clamp Electrophysiology.

Conventional whole cell recording techniques were used to directly measure the ability of test compounds to inhibit $Ca^{2+}$ current through N-type calcium channels. N-type current were recorded from both neuronally differentiated IMR- 32 cells, and native neurons freshly dissociated from superior cervical ganglia of early postnatal rats. Each day, currents in both cell types were confirmed as N-currents showing that greater than 90% of the total inward current during depolarizing steps was blocked by a supramaximal concentration (3 mM) of w-conotoxin MVIIA. Additionally, the potency of w-conotoxin MVIIA was periodically determined to be about 3 nM ($IC_{50}$), a value consistent with that reported in the literature. Results for a subset of compounds tested in both cell types did not differ significantly, thus data are considered as one data set unless otherwise specified.

A. IMR-32 Cell Culture and Differentiation:

IMR32 cells were cultured and neuronally differentiated using procedures identical to those described for the FLIPR N-channel assay except that for differentiation cells were plated in 35 mm plexiglass culture dishes, rather than 96-well plates.

B. Dissociation of Rat Superior Cervical Ganglion (SCG) Neurons:

7–10 day old rat pups were euthanized in a chamber containing a high $CO_2$ atmosphere. Immediately, SCG were surgically isolated, removed and placed in ice cold Hanks balance salt solution (HBSS). SCG's were desheathed, cut open and placed in a solution of HBSS containing 20 U/mL papain (37° C.) for 15 min. The papain solution was then exchanged for HBSS (37° C.) containing 16 mg/mL dispase and 400 U/mL collagenase for 40 min with gentle trituration of tissue every 15 min. Cells were then recovered by centrifugation and stored in 115 medium at 4° C. for use on the same day. For recording, a drop of cell containing solution was placed on a poly-L-lysine coated 35 mm plexiglass culture dish, and cells allowed to adhere for several minutes.

C. Electrophysiological Procedures:

Solutions: Recording solutions were adapted from those described by Thompson and Wong (1991) *J. Physiol.*, 439: 671–689. Solutions were stored as aliquots for not more than one month (intracellular, −20° C., extracellular, 4° C.) before experiments. The pipette (intracellular) solution contained (in mM): TRIS, 130; CsBAPTA, 10; HEPES, 10; $Mg^{2+}$ ATP, 5; pH to 7.3 with methanesulphonic acid; osmolality ~315 mOsm. Extracellular solution contained (in mM): TRIS 120; CsCl, 5; HEPES, 10; $Mg^{2+}Cl$, 1; $Ba^{2+}Cl$, 5, glucose, 25; tetraethylammonium chloride, 15; tetrodotoxin, 200 (added at time of experiment); pH to 7.4 with methanesulphonic acid; osmolality ~320 mOsm.

Whole cell recording and analysis: The whole-cell voltage clamp configuration of the patch clamp technique as described by Hamill et al. (1981) *Pflügers Arch.* 391: 85–100, was employed to isolate voltage-dependent calcium currents. Culture dishes containing cells were placed in a chamber on the stage of an inverted microscope. All experiments were conducted at room temperature (20–22° C.). Patch pipettes were fabricated from thin-wall glass (1.5 mm OD, 1.12 mm ID; World Precision Instruments, New Haven, Conn.) on the Brown-Flaming P-86 puller (DC resistance: 3–6 MΩ; Sutter Instr. Co., Novato, Calif.). An Axopatch 1B amplifier (Axon Instruments, Foster City, Calif.) was used to obtain current signals and this was connected to a personal computer by either a TL-1 (Scientific Solutions, Solon, Ohio) or Digidata 1200 (Axon Instr.) interface. The current signal was balanced to zero with the pipette immersed in the bath just prior to forming a seal on the neuron. Seal resistance ranged from 1 to greater than 10 GΩ. Series resistance was usually less than 10 MΩ, and was not compensated electronically. Digitized data acquisition and voltage step protocols were accomplished with pClamp 6.0 software (Axon Instr). Data were low-pass filtered at less than one-half the digital sampling rate prior to digitizing. To record N-type currents for evaluation of inhibitory potency of compounds (steady-state concentration-response analysis), 200 ms voltage steps to +10 mV were delivered at 15 sec intervals from a holding potential of −90 mV. The recorded currents were leak subtracted on-line with a P-4 or P-6 subpulse protocol in the pClamp software. To evaluate open channel block of compounds, 10 ms voltage steps to +10 mV were delivered at varying frequencies from a holding potential of −90 mV without using on-line leak subtraction. These voltage protocols both yielded constant inward current amplitudes over 5–10 minutes of recording. Peak current amplitude was analyzed using the clampfit module of pClamp software. Origin 5.0 software (Microcal Corp, Northampton, Mass.) was used to iteratively fit concentration-response data to a standard Hill function, and to provide graphic displays for current traces and analyzed data.

Drug/compound preparation and delivery: Test compounds were prepared as 10 mM stock solutions in DMSO, and appropriate volumes of these stock solutions dissolved into extracellular buffer to yield the desired concentrations. Solutions containing drugs/compounds were applied focally from any of six linearly arranged glass-lined tubes (200 mm o.d., Hewlett Packard, Wilmington, Del.) positioned ~100 mm from the recorded neuron. Each solution was released from the desired tube by an electronically controlled solenoid valve system (BME Systems, Baltimore, Md.). This system achieved rapid (<100 ms) equilibration of drug solution in the extracellular phase without perturbing the recording characteristics.

IV. Formalin Test.

The Formalin test is a well established pain test (Dubuisson and Dennis, 1977; Wheeler-Aceto et al., 1990; Coderre et al., 1993) which assesses the inhibitory effects of orally administered N-type calcium channel antagonists on formalin-induced nocifensive behaviours in rats. This test consists of two distinct phases of formalin-induced behaviour. The first phase response, occurring between 0 to 5 minutes, is caused by acute nociception to the noxious chemical (formalin) injected into the paw. This is followed by a quiescent period of between 5 to 15 min post injection. A second phase response, occurring after 15 minutes and lasting up to 60 minutes, is caused by sensitisation of the central neurons in the dorsal horn. Central sensitisation augments the noxious afferent input and a stronger pain barrage is transmitted into the brain. Inhibition of the second phase response is indicative of a central mechanism of drug action.

The procedure for the formalin test is as follows: male rats are placed in a plexiglass chamber and observed for 30–45 min. to observe their baseline activity. Multiple groups of animals are pretreated with either vehicle or different doses of a test compound. Animals are dosed with the drug of interest either 40 min., if by the intraperitoneal route, or 90 min., if by the oral route, prior to injection of formalin into a hind paw (under the dorsal skin; 0.05 mL of sterile 5% formalin). The number of paw flinches and licks during first phase (0–5 min.) and second phase (20–35 min.) are scored and recorded. Flinch and lick responses are calculated as percentage of inhibition compared with the mean score of a saline control group. Drug potencies are expressed as the dose which causes 50% of the maximum inhibitory effect ("$ID_{50}$"). Student t-tests are used for statistical analysis to determine the significance of drug effects. Compounds are considered active based on their ability to inhibit the flinch response.

V. Chronic Constrictive Injury Test.

The Chronic Constrictive Injury ("CCI") test or Neuropathic Pain Model assesses neuropathic pain associated with nerve injuries that can arise directly from trauma and compression, or indirectly from diseases ranging from infection to cancer, metabolic conditions, toxins, nutritional deficiencies, immunological dysfunction and musculoskeletal changes. In the CCI model (Bennett and Xie, 1988) a unilateral peripheral neuropathy is produced in rats by partial nerve ligation.

Sprague-Dawley rats (250–350 g) are anesthetized with sodium pentobarbital and the common sciatic nerve is exposed at the level of the mid thigh by blunt dissection through the biceps femoris. A section of nerve (about 7 mm), proximal to the sciatic trifurcation, is exposed and ligated 4 times with chromic gut suture. The suture is tied with about 1 mm spacing between ligatures. The incision is closed in layers and the animals are allowed to recover. Thermal hyperalgesia is measured using the paw-withdrawal test (Hargreaves et al, 1988). Nerve compression due to the partial nerve ligation causes'shorter latencies for paw withdrawal compared to the latency of paw withdrawal of paws of normal or sham operated legs. Animals are habituated on an elevated glass floor. A radiant heat source is aimed at the mid-plantar hindpaw (sciatic nerve territory) through the glass floor with a 20 second cut-off used to prevent injury to the skin. Latencies for the withdrawal reflex in both paws are recorded. Response to test compounds are evaluated at different times following oral administration to determine onset and duration of drug effect. Dose response studies are conducted with multiple groups of CCI rats dosed orally with either vehicle or the test compound for 5 days. Paw withdrawal latencies are measured each day prior to the first daily dose. Data analysis is performed by multiple means comparison (Dunnett's test) and drug potencies are expressed as the dose which causes 50% of the maximum efficacy ("$EC_{50}$").

Compounds of the invention generally bind to N-type calcium channels with $IC_{50}$'s, measured in the FLIPR assay described herein of about 10 μM or less. For example, compounds of Examples 12, 13, 14, 15 and 16, respectively exhibit $IC_{50}$'s of 10.53, 8.60, 8.82, 5.38 and 5.78.

Exemplary Chemical Method:

The following method describes the preparation of 6-(3,5-Dichlorophenyl)-2-(3-fluorophenyl)-N-methyl-4-quinolinamine, the compound of Example 17, below. Other compounds exemplified herein were prepared by procedures analogous to those described heretofore from suitable substituted-acetophenone and substituted-boronic acid precursors.

3-(3-Fluorophenyl)-3-oxo-propionic acid ethyl ester:

Into a three-neck 2 L round-bottom flask equipped with an addition funnel, nitrogen inlet, magnetic stirrer, heating mantle, thermocouple and condenser, was placed 21.7 g (0.543 moles) of a 60%-in-oil dispersion of sodium hydride. To this was added 1 L dry hexane and the resulting suspension was stirred for 15 minutes. Stirring was halted and the solids were allowed to settle and the clear supernatant containing the hexane and dissolved oil was then removed via a cannula. Diethyl carbonate (1 L) was added to the solids and the suspension was heated to 120° C. To the hot suspension was cautiously added dropwise, over 40 minutes, a solution of 100 g (0.494 moles) of m-fluoro acetophenone dissolved in 250 mL of diethyl carbonate. As addition proceeded a reaction initiated, hydrogen was evolved and the color changed to tan. After the acetophenone-derivative addition was complete, the reaction was heated for 1 additional hour. The reaction mixture was cooled and was poured into a 2 L separatory funnel. The diethyl carbonate layer was twice washed with 10% acetic acid solution, dried over $MgSO_4$ and filtered. The product was purified by vacuum distillation (bp 114–117° C. at 0.8–0.9 mm Hg) in 91% yield.

3-(4-Bromo-phenylamino)-3-(3-fluorophenyl)-acrylic acid butyl ester:

Into a 1 liter single-neck round-bottom flask equipped with a Soxhlet extractor apparatus with condenser, magnetic stirrer and nitrogen inlet was placed 50.25 g (0.183 moles) of 3-(4-cyclohexyl-phenyl)-3-oxo-propionic acid ethyl ester, 25 g (0.167 moles) of 4-bromoaniline, 1.55 g (0.008 moles) 4-bromoaniline hydrochloride salt and 500 mL of dry n-butanol. Into the Soxhlet thimble (33×118 mm) was placed highly activated 4 Å sieves (1.7–2.4 mm beads). These sieves are activated immediately before use under high vacuum with heating (400° C. for 30 min). The mixture was then brought to reflux such that the butanol azeotropically removed water, driving the equilibrium reaction, and the water was removed from the butanol by the sieves before being returned to the reaction pot. The reaction was allowed to continue for 48 hrs. It was necessary to replace the charge of sieves after the first 24 hrs. Transesterification to the butyl ester along with removal of ethanol occurs concomitantly with enamine formation. After 48 hrs the reaction pot was cooled, then placed in a −40° C. freezer and crystals were allowed to form over 24 hrs. The crystals were collected by vacuum filtration and the solids washed with cold ethanol. The product was then dried in a vacuum oven to give 73.8 g (98%) of the desired enanine.

6-Bromo-2-(3-fluorophenyl)-quinolin-4-ol:

To a 3 L three-neck flask, equipped with mechanical stirrer, Claisen adapter holding a thermocouple probe and reflux condenser with nitrogen inlet was added 0.75 L of Dowtherm A (a eutectic mixture of 26.5% diphenyl and 73.5% diphenyl oxide) and the solvent was heated to 250° C. To this was cautiously added in small portions 77.0 grams (0.215 moles) of 3-(4bromo-phenylamino)-3-(3-fluorophenyl)-acrylic acid butyl ester over the course of 0.25 hours. The mixture was maintained at 250° C. for 1.5 hours and then allowed to cool to 90° C. over the course of 2 hours. The mixture was treated with 1.0 L of hexanes, and allowed to cool to room temperature while stirring overnight. The tan solids were collected by suction filtration and washed with three 0.15 L portions of hexanes. The solids were dried under vacuum at 50° C. overnight to yield 58.63 grams (96.0%) of the title compound.

6-Bromo-4chloro-2-(3-fluorophenyl)-quinoline:

Into a 500 mL three-neck round-bottom flask equipped with a condenser, magnetic stirrer and nitrogen inlet was placed 5.2 g (16.3 mmoles) of 6-bromo-2-(3-fluorophenyl)-quinolin-4-ol. To this was added 15.2 mL (25.0 g, 163 mmoles, 10 equiv.) of phosphorus oxychloride with stirring. The mixture was heated to 110° C. for 4 hr. At the end of this time the reaction was cooled to room temperature and water was cautiously added dropwise until all of the $POCl_3$ was consumed. The product crystallised from the water and solids were collected by filtration. The solids were washed with water, placed in a 250 mL Erlenmeyer and triturated with water. After collection by filtration, washing with water, and drying in a vacuum oven, 4.6 g (84%) of the product was obtained.

N-[6-Bromo-2-(3-fluorophenyl)-4-quinolinyl]-N,N-dimethylamine:

Into a 500 mL three-neck round-bottom flask equipped with magnetic stirrer, nitrogen inlet, gas outlet, condenser and heating bath was placed 20 g (59.4 mmoles of 6-bromo-4-chloro-2-(3-fluorophenyl)-quinoline. The material was dissolved in 150 mL of N-methyl pyrrolidinone and 250 mL of a 40% aq. solution of dimethylamine was added to the stirring mixture. The reaction was then warmed to 60° C. for 48 hrs. At the end of this time the reaction was cooled, into 3 L of water in a 4 L Erlenmeyer flask and the mixture was stirred until solids formed. The solids were collected by vacuum filtration and dried in a vacuum oven. The product was recrystallised from ethanol in a −20° C. freezer to give 19.6 g (95%) yield of the aminated product.

N-[6-bromo-2-(3-fluorophenyl)-4-quinolinyl]-N,N-dimethylamine was alternatively prepared as follows. Into a 1 L Parr bomb equipped with mechanical stirring, thermocouple, heater with controller and pressure gauge was placed 20 g (59.4 mmoles of 6-bromo-4-chloro-2-(3-fluorophenyl)-quinoline. To this was added 350 mL of ethanol and 350 mL of a 40% aq. solution of dimethylamine. The bomb was sealed and the stirred mixture was then heated to 100° C. resulting in a pressure of approximately 15.0 psi. Heating was continued for 24 hrs. At the end of this time the reaction was allowed to cool to room temperature and was then vented. The contents were then poured into 3 L of water in a 4 L Erlenmeyer flask and the mixture was stirred until solids formed. The solids were collected by vacuum filtration and then dried in a vacuum oven. The crude product was recrystallised from ethanol in a −20° C. freezer to give 18.15 g (92%) yield of the aminated product.

6-(3.5-Dichlorophenyl)-2-(3-fluorophenyl)N-methyl-4-quinolinamine:

To 0.4 g. (1.2 mmole) of N-[6-bromo-2-(3-fluorophenyl) 4-quinolinyl]-N-methylamine was added 0.275 g. (1.45 mmole) of 3,5-dichlorophenylboronic acid and a catalytic amount of tris(dibenzylideneacetone)dipalladium (0), 0.0109 g. (0.012 mmole). The mixture was dissolved in 7 mL of N-methyl-2-pyrrolidinone. Sodium carbonate, 0.105 g. (1.45 mmole) was dissolved in a minimal amount of water and added in one portion to the N-methyl-2-pyrrolidinone reaction solution. The mixture was heated to 80° C. for 10 hours. After cooling to room temperature, the mixture was diluted to 10 mL total volume with methanol and filtered through a silica plug. The title compound was isolated by reverse phase HPLC on a 2 inch Dynamax phenyl column using a solvent gradient from 85:15 methanol:water to 100% methanol, yield 0.320 g. (67%).

EXAMPLES

Exemplary compounds 1 to 22, inclusive, are disclosed in Table 1 which shows the name of each compound, the molecular formula and the mass spectroscopy result determined for the particular compound.

TABLE 1

| Ex. | Name | Molecular Formula | M + 1 |
|---|---|---|---|
| 1 | 2-(3-fluorophenyl)-6-(4-fluorophenyl)-4-dimethylaminoquinoline | $C_{23}H_{18}F_2N_2$ | 361(+) |
| 2 | 2-(3-fluorophenyl)-6-(4-methoxyphenyl)-4-dimethylaminoquinoline | $C_{24}H_{21}FN_2O$ | 373(+) |
| 3 | 2-(3-fluorophenyl)-6-(1,3-benzodioxol-5-yl)-4-dimethylaminoquinoline | $C_{24}H_{19}FN_2O_2$ | 387(+) |
| 4 | 2-(3-fluorophenyl)-6-(3-ethan-1-onyl-phenyl)-4-dimethylaminoquinoline | $C_{25}H_{21}FN_2O$ | 385(+) |
| 5 | 2-(3-fluorophenyl)6-(2,4-difluorophenyl)-4-dimethylaminoquinoline | $C_{23}H_{17}F_3N_2$ | 379(+) |
| 6 | 2-(3-fluorophenyl)-6-(4-methylphenyl)-4-dimethylaminoquinoline | $C_{24}H_{21}FN_2$ | 357(+) |
| 7 | 2-(3-fluorophenyl)-6-(3,4,5-trimethoxyphenyl)-4-dimethylaminoquinline | $C_{26}H_{25}FN_2O_3$ | 433(+) |

TABLE 1-continued

| Ex. | Name | Molecular Formula | M + 1 |
|---|---|---|---|
| 8 | 2-(3-fluorophenyl)-6-[3-(trifluoromethyl)phenyl]-4-dimethylamnioquinoline | $C_{24}H_{18}F_4N_2$ | 411(+) |
| 9 | 2-(3-fluorophenyl)-6-(2-methylphenyl)-4-dimethylaminoquinoline | $C_{24}H_{21}FN_2$ | 357(+) |
| 10 | 2-[4-(dimethylamino)-2-(3-fluorophenyl)-6-quinolinyl]-benzaldehyde. | $C_{24}H_{19}FN_2O$ | 371(+) |
| 11 | 2-(3-fluorophenyl)-6-(2-ethoxyphenyl)-4-methylaminoquinoline | $C_{24}H_{21}FN_2O$ | 373(+) |
| 12 | 2-(3-fluorophenyl)-6-(2-chlorophenyl)-4-methylaminoquinoline | $C_{22}H_{16}ClFN_2$ | 363(+) |
| 13 | 2-(3-fluorophenyl)-6-phenyl-4-methylaminoquinoline | $C_{22}H_{17}FN_2$ | 329(+) |
| 14 | 2-(3-fluorophenyl)-6-(2-methylphenyl)-4-methylaminoquinoline | $C_{23}H_{19}FN_2$ | 343(+) |
| 15 | 2-[2-(3-fluorophenyl)-4-(methylamino)-6-quinolinyl]-benzaldehyde | $C_{23}H_{17}FN_2O$ | 357(+) |
| 16 | 2-(3-fluorophenyl)-6-(2-methoxyphenyl)-4-methylaminoquinoline | $C_{23}H_{19}FN_2O$ | 359(+) |
| 17 | 2-(3-fluorophenyl)-6-(3,5-dichlorophenyl)-4-methylaminoquinoline | $C_{22}H_{15}Cl_2FN_2$ | 397/399(+) |
| 18 | 2-(3-fluorophenyl)-6-(1,3-benzodioxol-5-yl)-4-methylaminoquinoline | $C_{23}H_{17}FN_2O_2$ | 373(+) |
| 19 | 2-(3-fluorophenyl)-6-(4-fluorophenyl)-4-methylaminoquinoline | $C_{22}H_{16}F_2N_2$ | 347(+) |
| 20 | 2-(3-fluoro-phenyl)-6-(3-chloro-5-methyl-phenyl)-4-methylaminoquinoline | $C_{23}H_{18}ClFN_2$ | 377/379(+) |
| 21 | 2-(3-fluorophenyl)-6-(4-chlorophenyl)-4-methylaminoquinoline | $C_{23}H_{18}ClFN_2$ | 377/379(+) |
| 22 | 2-phenyl-6-phenyl-4-pheneth-2-ylaminoquinoline | $C_{29}H_{24}N_2$ | 401(+) |

What is claimed is:
1. Any compound in accord with structural diagram I,

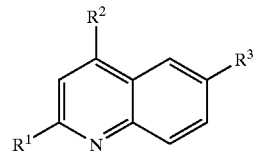

wherein:
R$^1$ is halophenyl;
R$^2$ is NE$^1$E$^2$ where E$^1$ is selected from hydrogen and C$_{1-3}$alkyl and E$^2$ is selected from C$_{1-3}$alkyl and (CH$_2$)$_n$phenyl where n is selected from 1, 2 or 3, and
R$^3$ is selected from phenyl, 1,3-benzodioxolyl and phenyl substituted with one, two or three moieties independently selected from halo, C$_{1-3}$alkyl, perhaloC$_{1-3}$alkyl, HC(O)—, C$_{1-3}$alkoxy and C$_{1-3}$alkylcarbonyl.
2. A compound according to claim 1, wherein:
R$^1$ is fluorophenyl;
R$^2$ is NE$^1$E$^2$ where E$^1$ is selected from hydrogen and methyl, and E$^2$ is methyl, and
R$^3$ is selected from phenyl, 1,3-benzodioxol-5-yl and phenyl substituted with one, two or three moieties independently selected from chloro, fluoro, methyl, ethyl, methoxy, ethoxy, trifluoromethyll, HC(O)—, and CH₃C(O)—.

3. A compound according to claim 2, wherein:
R¹ is 3-fluorophenyl;
R² is NE¹E² where E¹ is selected from hydrogen and methyl, and E² is methyl, and
R³ is selected from phenyl, 1,3-benzodioxol-5-yl and phenyl substituted with one, two or three moieties independently selected from chloro, fluoro, methyl, ethyl, methoxy, ethoxy, trifluoromethyll, HC(O)—, and CH₃C(O)—.

4. A method for treating pain, said method comprising administering a pain-ameliorating effective amount of a compound according to claim 1.

5. A method according to claim 4, comprising administering a pain-ameliorating effective amount of a compound to a subject in need of treatment for acute, persistent or neuropathic pain.

6. A method for making compounds according to claim 1, said method comprising:

a) reacting a substituted acetophenone according to structural diagram II with acetic anhydride carbonic acid diethyl ester and sodium hydride to form a 3-substituted-3-oxo-propionic acid ethyl ester according to structural diagram III, as follows:

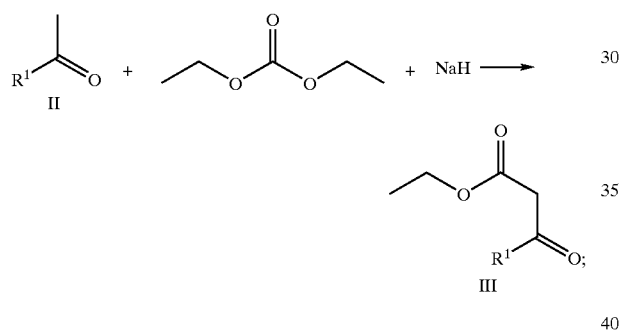

b) reacting a 3-substituted-3-oxo-pronionic acid ethyl ester compound of structural diagram III with 4-bromoaniline in acidic butanol in the presence of 4A sieves and heat to form a 3-substituted 3-(4-bromophenylamino)acrylic acid butyl ester according to structural diagram IV, as follows:

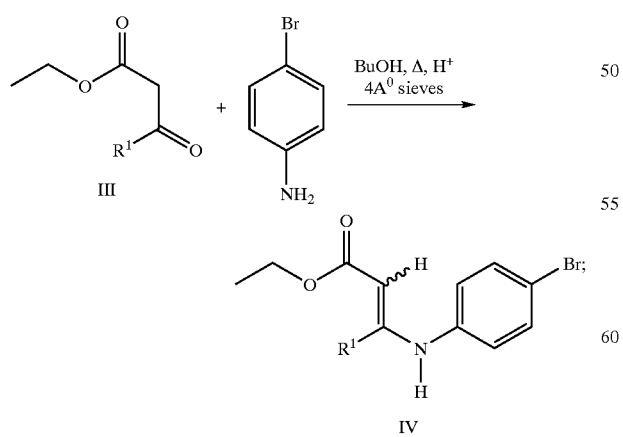

c) cyclizing a 3-substituted 3-(4-bromophenylamino) acrylic acid butyl ester compound of structural diagram IV in the presence of Dowtherm and heat to form a 2-substituted 6-bromo-4-hydroxy-quinoline according to structural diagram V, as follows:

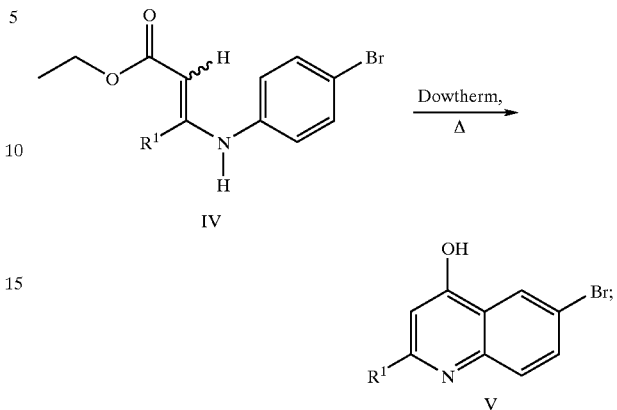

d) chlorinating a 2-substituted 6-bromo-4-hydroxy-quinoline compound of structural diagram V in the presence of phosphorus oxychloride to form a 2-substituted 6-bromo-4-chloro-quinoline compound according to structural diagram VI, as follows:

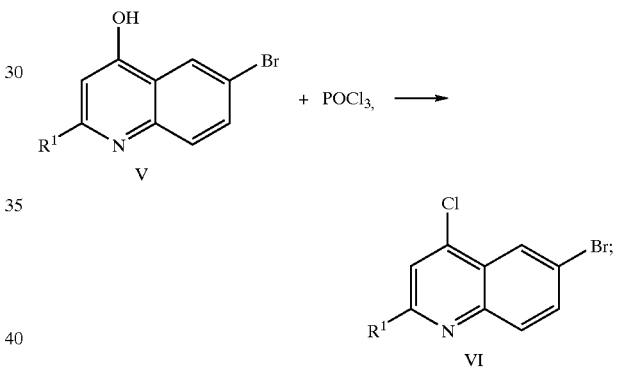

e) selectively replacing the chlorine moiety of a 2-substituted 6-bromo-4-chloro-quinoline compound of structural diagram VI by reacting it with an R2H compound with heat in N-methyl pyrrolidinone to form a 2,4-disubstituted 6-bromo-quinoline compound according to structural diagram VII, as follows:

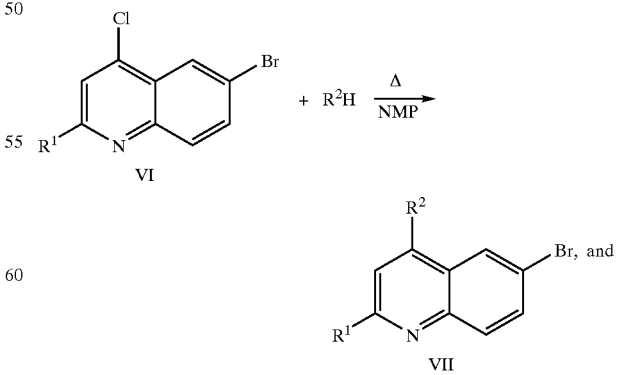

f) selectively replacing the bromine moiety of a 2,4-disubstituted 6-bromo-quinoline compound of structural diagram VII by reaction with a substituted boronic acid in the presence of a palladium catalyst in N-methyl pyrrolidinone with heat to form a 2,4,6-trisubstituted-quinoline compound according to structural diagram I, as follows:

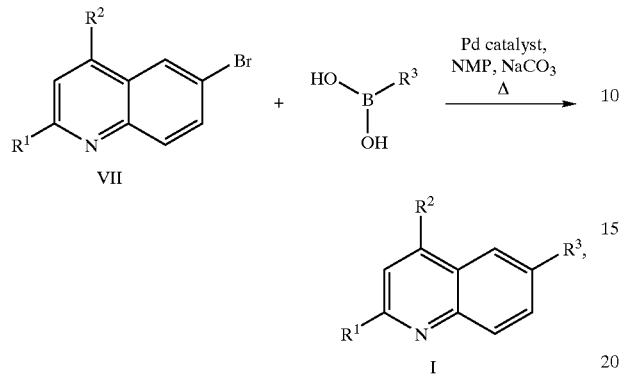

wherein $R^1$, $R^2$ and $R^3$ are as defined in claim 1;

wherein, if necessary, in steps a), b), c), d), e) and f) any functional group is protected with a protecting group, and thereafter, g) removing any said protecting group;

h) converting one compound according to structural diagram I to another compound according to structural diagram I, and i) purifying said compound of structural diagram I to the extent necessary and, if necessary, forming a pharmaceutically-acceptable salt.

7. A pharmaceutical composition for the treatment of acute, persistent or neuropathic pain comprising a compound according to claim 1 together with one or more additives selected from excipients, diluents or stabilisers.

* * * * *